United States Patent
Al-Saggaf et al.

(10) Patent No.: US 11,642,067 B1
(45) Date of Patent: May 9, 2023

(54) SYSTEM AND METHOD FOR UNSUPERVISED ADAPTIVE THRESHOLD NEUROFEEDBACK TREATMENT

(71) Applicant: King Abdulaziz University, Jeddah (SA)

(72) Inventors: Ubaid M. Al-Saggaf, Jeddah (SA); Mohammed U Alsaggaf, Jeddah (SA); Muhammad Moinuddin, Jeddah (SA); Syed Saad Azhar Ali, Seri Iskandar (MY); Sulhi Ali Alfakeh, Jeddah (SA); Yasir Hafeez, Seri Iskandar (MY)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/819,776

(22) Filed: Aug. 15, 2022

(51) Int. Cl.
| | |
|---|---|
| A61B 5/00 | (2006.01) |
| A61B 5/372 | (2021.01) |
| A61B 5/375 | (2021.01) |
| A61B 5/31 | (2021.01) |
| A61N 1/36 | (2006.01) |
| A61B 5/374 | (2021.01) |

(52) U.S. Cl.
CPC ............ *A61B 5/375* (2021.01); *A61B 5/31* (2021.01); *A61B 5/374* (2021.01); *A61B 5/7278* (2013.01); *A61N 1/36082* (2013.01)

(58) Field of Classification Search
None
See application file for complete search history.

(56) References Cited

U.S. PATENT DOCUMENTS

| 11,116,440 B2 | 9/2021 | Prat et al. |
| 11,154,234 B2 | 10/2021 | Barthelemy et al. |
| 2015/0351655 A1 | 12/2015 | Coleman |
| 2017/0071532 A1* | 3/2017 | Greco .................. A61B 5/318 |

(Continued)

FOREIGN PATENT DOCUMENTS

| DE | 10 2018 118 277 A1 | 1/2020 |
| EP | 3 181 043 A1 | 6/2017 |

OTHER PUBLICATIONS

Lansbergen et al. ADHD and EEG-neurofeedback: a double-blind randomized placebo-controlled feasibility study. Journal of Neural Transmission (2011) 118:275-284. (Year: 2011).*

*Primary Examiner* — Etsub D Berhanu
(74) *Attorney, Agent, or Firm* — WCF IP (57) ABSTRACT

Examples include receiving and storing samples of target frequency bands filtered from EEG measurement of a subject's brain waves in an NFB training session. In an example, upon storing a time window of the samples, unsupervised adaptive adjusting an NFB reward threshold is automatic. The adjusting includes, in examples, determining neuromarker values in the time window, which indicate peak values of the target frequency bands over the time window. The adjusting computes the mean value of the neuromarker values and, utilizing same, automatically proceeds to unsupervised computing an adaptive adjusted reward threshold. The unsupervised computing, in examples, includes a multiplication product of a reward threshold adjustment factor, a training protocol value, and the computed mean value of the neuromarker values. Examples proceed to communicating the adaptive adjusted reward threshold to a controller for threshold based feedback reward to the NBF subject.

7 Claims, 5 Drawing Sheets

(56) References Cited

U.S. PATENT DOCUMENTS

| | | | |
|---|---|---|---|
| 2017/0347906 A1* | 12/2017 | Intrator | A61B 5/375 |
| 2018/0263553 A1* | 9/2018 | Spiluttini Hebert | A61B 5/4809 |
| 2018/0368719 A1* | 12/2018 | Prat | A61B 5/316 |
| 2020/0330033 A1 | 10/2020 | Kusik et al. | |

* cited by examiner

Fig. 6

SYSTEM AND METHOD FOR UNSUPERVISED ADAPTIVE THRESHOLD NEUROFEEDBACK TREATMENT

BACKGROUND

Technical Field

Embodiments generally relate to systems and methods of neurofeedback therapy and, in particular, to neurofeedback therapy using computer-based adjusting of reward threshold.

Description of Related Art

Neurofeedback (NFB) is a non-invasive biofeedback reward-based technique for training a subject to consciously change certain characteristics of the subject's electro-encephalogram (EEG) brainwaves. The brainwaves of the subject prior to undertaking NFG treatment may have characteristics, e.g., time-amplitude characteristics or power spectral density patterns, that differ from normal templates, and/or align with signature characteristics of certain neurophysiological conditions such as, for example, anxiety or depression, as well as attention deficit hyperactivity disorder (ADHD), epilepsy.

Generally, NFB training sessions include conductive attachment of an EEG device's sensors to particular areas of the subject's scalp, then detecting the differences between characteristics of specific frequency bands of the subject's EEG measured brainwave pattern, e.g., power spectral density, and a template of a normal EEG pattern, for the particular area of the subject's scalp. Based on the detecting a feedback is generated and based on same, a feedback stimulus, e.g. audio, visual audiovisual, or tactile, is delivered or withdrawn from, or not delivered to the subject. The feedback reward stimuli can be of various types. Examples include subjectively interesting, calming, or pleasing audiovisual content.

Neurofeedback training can assist subjects in attaining a desired balance in activity levels in or among specific areas of the subject's brain, for purposes of attaining activity levels that better align, for example, with databases of various normal patterns of brain area activity. NFB subjects, through willful feedback assisted efforts to change certain brain area activities, can reduce, ameliorate, or even eliminate various Measures of efficacy of the NFB training include the number training sessions needed for the subject to attain the desired end state EEG characteristics, e.g., alignment with or within an acceptable range or vector distance from a normal template.

A factor of particular importance is the selection, and in-session adjustment of a reward threshold, i.e., the magnitude of incremental change in a subject's relevant brain wave(s), toward a desired brainwave state, that the system must detect to trigger the sending of the reward to the subject. e.g., continuing a video presentation.

However, current techniques have shortcomings regarding initial selection and further shortcomings regarding in-session adjustment of the threshold. Common to both initial selection and in-session adjustment the considerable dependance on the skill level and judgment of a practitioner. This dependance has costs, including variance in treatment efficacy due to unintentional biases in practitioner judgment, variance in practitioner skill, scarcity of NFB treatment resources, and increased cost of treatment due to insufficient numbers of skilled practitioners. A cost more particular to in-session adjustment is that the action can interrupt the session, can be experienced as annoying or intrusive by the subject.

SUMMARY

This Summary identifies example features and aspects and is not an exclusive or exhaustive description of disclosed subject matter. Whether features or aspects are included in or omitted from this Summary is not intended as indicative of relative importance of such features or aspects. Additional features are described, explicitly and implicitly, as will be understood by persons of skill in the pertinent arts upon reading the following detailed description and viewing the drawings, which form a part thereof.

According to one or more embodiments, an example method for unsupervised adaptive threshold neurofeedback (NFB) training can include a processor receiving and storing a time window of samples of target frequency bands from an electroencephalogram (EEG) measuring of brain wave signals of a subject in an NFB training session and based at least in part on the stored time window of samples performing an unsupervised adaptive adjustment of an NFB reward threshold. The example includes steps of determining neuromarker values in the time window of samples, based at least in part on peak values of the target frequency bands over the time window, computing the mean value of the neuromarker values over the time window, computing an adaptive adjusted NFB reward threshold, based at least in part on a multiplication product of a reward threshold adjustment factor, a training protocol value, and the computed mean value of the neuromarker values, and communicating the computed adaptive adjusted NFB reward threshold to an NFB controller. The example can include the NFB controller using the computed adaptive adjusted NFB reward threshold as a reward feedback threshold for contingent delivery-non delivery of a feedback reward to the subject.

According to one or more embodiments, an example system for unsupervised adaptive threshold NFB training can include a processor, connected by a bus to a data memory and to an instruction memory, the instruction memory comprising a non-volatile tangible storage medium, stored in the instruction memory, processor executable instructions that cause the processor to perform a method, the method comprising processor steps that include in response to receiving samples of target frequency bands filtered from an EEG measurement signal stream from an EEG device measuring brain signals of a subject in an NFB training session and storing, in the data memory a time window of the samples, determining neuromarker values in the time window of samples, based at least in part on peak values of the target frequency bands over the time window, computing the mean value of the neuromarker values over the time window, computing an adaptive adjusted NFB reward threshold, based at least in part on a multiplication product of a reward threshold adjustment factor, a training protocol value, and the computed mean value of the neuromarker values, and communicating the computed adaptive adjusted NFB reward threshold to an NFB controller.

DETAILED DESCRIPTION

It will be understood that the term "adjust," and grammar variants thereof, e.g., "adjusting, "adjustment," as used herein in the context of the threshold for delivery—non delivery of the reward stimulus to the subject of the NFB training, also encompasses, but is not limited to, "select, set, change, update, adapt, instantiate, replace, renew, modify, substitute for, vary, alter, and increment" and grammar variants of each, except where explicitly stated or made clear from the context to mean otherwise.

Systems according to various embodiments comprise functional blocks that perform, in combination, in real time during a subject's NFB sessions, novel adaptive adjusting of the feedback reward threshold that can obviate the current general NFB requirement for in-session observation and corresponding manual, intervening adjustment of the threshold by a skilled practitioner. Features and advantages of embodiments' real time, in-session, adaptive adjusting of the feedback reward threshold further include, without limitation, substantive improvement in NFB training efficacy.

Example implementations of systems according to various embodiments comprise, as functional processing blocks, collecting of relevant frequency bands of EEG measurement of the subject's brainwaves, time windowing of the samples of the relevant frequency bands, and, using the time windows of the samples, performing novel unsupervised, inherently adaptive adjustment. According to various embodiments, the time window can be a running time window having a width of, for example, integer G samples.

Processes in the adaptive adjustment, according to various embodiments, include detecting or extracting particular neuromarkers, combined with computing of mean values of the neuromarkers over the time window. The neuromarkers, in one or more embodiments, comprise peak amplitudes of target frequency bands over the time window. According to various embodiments, processes in the novel adaptive adjusting include arithmetic multiplying the mean of the neuromarker, e.g., the mean of the peak amplitudes of the target frequency bands, by a factor indicating whether the FNB training is an up training or a down training, and by a weight factor that scales the amount of each adjustment to the threshold.

According to one or more embodiments, the unsupervised, adaptive adjusting of the feedback reward threshold can be performed at every increment of the time window. The increment can be, for example, integer K of the samples of the relevant frequency bands. The integer K may, for example, be equal to G and in such a configuration the supervised, adaptive adjusting of the feedback reward threshold is performed, automatically, every G samples. In other embodiments, K can be less than G, and in such configuration the running time window can be a sequence of partially overlapping windows of G width, and the supervised, adaptive adjusting of the feedback reward threshold can be performed, automatically, every K samples. The processor can be, e.g. and without limitation, a processor of a particularly configured general purpose programmable computer. The configuration can be implemented, for example, by particular configured executable instructions stored, e.g., in a non-volatile tangible instruction memory connected to the processor that cause the processor to perform according to the described process flow. To focus on concepts and features particular to disclosed embodiments, various of the following descriptions of example steps and operations flows may omit explicit description of arrangements and structured of executable instructions. In such instances, implementations and arrangements of the instructions, can be, but are not necessarily in accordance with the non-limiting example "module" arrangement described in more detail in reference to the appended FIG. 6.

Example 1

Figure 1:
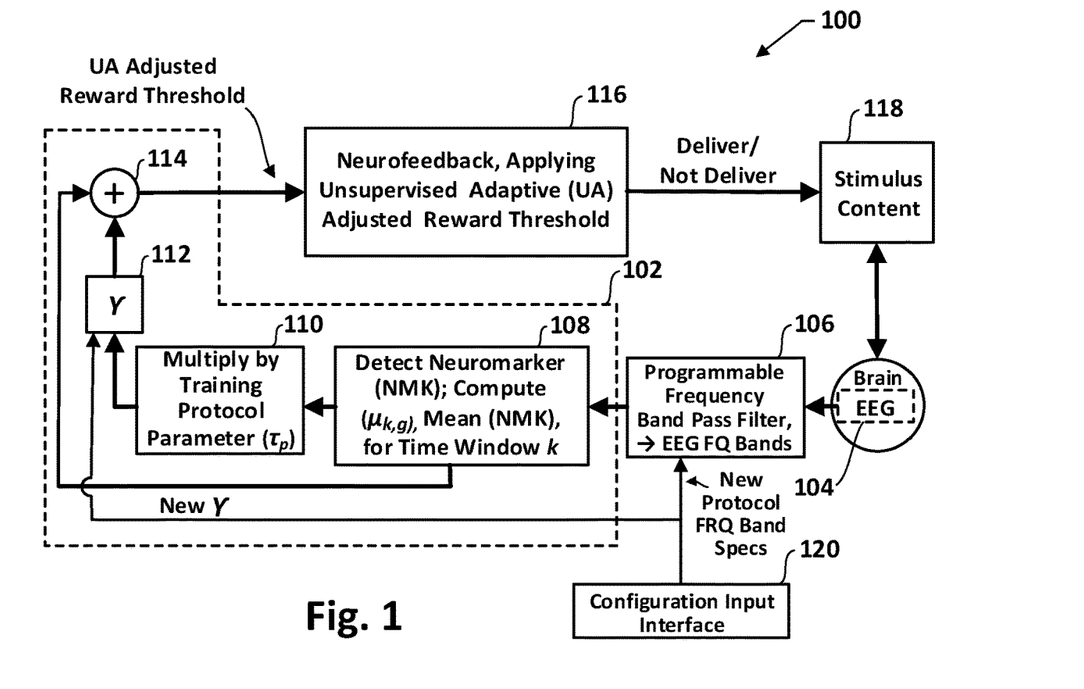
FIG. 1 is a functional block diagram of one example configuration of an NFB system featuring unsupervised adaptive threshold selection in accordance with one or more disclosed embodiments.

FIG. 1 is a functional block diagram of an example system and of certain process flows on same, in accordance with various embodiments, collectively "system 100." Features of the system 100 include unsupervised adaptive adjusting, using processes in accordance with various emblements, real-time, in-session, of the NFB training subject's reward threshold. The adjusting can include unsupervised adaptive initialization of the reward threshold. Such initialization can be based, at least in part, on pre-session EEG measurement of the subject, in a rest, eyes open state. Further features provided by systems according to various embodiments, such as system 100 and various modifications of same that persons of skill in the NFB arts, having possession of this disclosure, can readily make, include transparency to the subject, e.g., no interruption of the session and no other subject-discernible operation or action, and a substantial lessening instead of adding to the practitioner's in-session workload.

The FIG. 1 system 100 comprises an unsupervised adaptive threshold adjustment logic 102 featuring resources for receiving, during a subject's NFB training, relevant EEG frequency bands from an EEG device 104 measuring of the subject's brainwaves. The arrangement for the EEG measuring by can include a selection of the EEG device 104 EEG sensor pads being conductively attached to a respective set of surface areas of the subject's head. For purposes of description the relevant brainwave frequency bands will be referenced as "EEG target frequency bands." Also for purposes of description, the word sequence "unsupervised adaptive" will be alternatively recited as "UA," which is an arbitrary abbreviated form having no intrinsic meaning.

Processes of obtaining the EEG target frequency bands can be performed by a bandpass filtering function, having configurable filtering parameters, such as the FIG. 1 example programmable frequency bandpass filter 106. Alternatively, such bandpass filtering can be performed by logic, e.g., particularly configured processing resources, in the UA threshold adjustment logic 102.

Functional processing blocks of the UA threshold adjustment logic 102 can include logic, such as indicated by the FIG. 1 functional block 108, for detecting or extracting particular neuromarkers and for computing mean values of the neuromarkers over the time window. FIG. 1 block 108 labels these operations, as in abbreviated form, as "Detect Neuromarker (NMK); Compute (μ k,G) Mean (neuromarker) for Time Window k." The neuromarkers, in one or more embodiments, can comprise peak amplitudes of target frequency bands over the time window.

On FIG. 1 block 108, the mean neuromarker is represented as $\mu_{k,G}$, i.e., the mean of the average peak amplitude, fit, of the target frequency EEG band over the most recent content state, indicated by "k" index, of the moving window of G samples.

In various embodiments, further process blocks in the UA threshold adjustment logic 102 can include a block for arithmetic multiplying the mean of the neuromarker, e.g., the mean of the peak amplitudes of the target frequency bands, by a training protocol parameter $\tau_p$ that indicates whether the FNB training is an up training or a down training, and a block for multiplying by a by a weight factor that scales the amount of each adjustment to the threshold.

On the FIG. 1 graphical schematic, block 110 represents multiplying mean of the neuromarker by the training protocol parameter $\tau_p$ and block 112 represents multiplying by weight, i.e., change factor $\gamma$ that scales the amount of each adjustment to the threshold.

Referring to FIG. 1, the above-described operations of functional process blocks 110 and 112, in combination with the arithmetic summing block 114, adaptively adjust the reward feedback threshold according to the following Equation 1:

$$T_{k+g} = (1+\tau_p \gamma)\mu_{k,g} \quad \text{Equation (1)}$$

where $T_{k+g}$ represents the adaptive threshold at time instant k for the forward-moving window of size g.

According to various embodiments the training protocol parameter $\tau_p$ can be defined according to the following Equation (2):

$$\tau_p = \begin{cases} +1, & \text{for up-training} \\ -1, & \text{for down-training} \end{cases} \quad \text{Equation (2)}$$

In one or more embodiments, the change factor $\gamma$ is the factor by which the threshold is adjusted higher or lower than the neuromarker $\mu_{k,g}$.

According to various embodiments, the UA threshold adjustment logic 102 can be further configured, e.g., by a particular combination of executable instruction in an instruction memory of a processor, such as the FIG. 6 example described in more detail later, to select or instantiate an initial threshold, $T_0$, at k=0, g=0, by a specific iteration or instance of the above described adjustment process that uses, as the EEG frequency band samples, samples from an eyes-open resting-state session prior to the actual NFB training session, such as defined by the following Equation (3):

$$T_0 = (1+\tau_p \gamma)\mu_0 \quad \text{Equation (3)}$$

where $\mu_0$ is the average peak amplitude of target frequency EEG band in eyes-open res in-state.

Referring to FIG. 1 block 108, an example implementation of the described running time window can be as a shift-in-shift-out content of a G-sample width register or buffer in a data memory.

Referring to FIG. 1, system 100 can include a computational resource 116 that can be configured to perform processes that include generating, based on comparing a relevant measure of the NFB subject's current EEG target frequency characteristics against the current threshold value, $T_k$, a deliver-non deliver command to a reward stimulus delivery device 118, which can be positioned and arranged within a relevant sensory space surrounding the subject. The reward stimulus delivery device 118 may be, for example, an audiovisual display, or of another type for other reward stimulus modalities.

The reward stimulus delivery device 118, in response to the deliver—not deliver command, switches between delivering and not delivering the feedback reward, e.g., maintaining or termination display of an audiovisual content. The current threshold value, $T_k$, is the feedback reward threshold as adaptively adjusted using the previous time window of samples, e.g., the k−1 time window. The metric or characteristic of the subject's current EEG can be, for example, the mean neuromarker value computed by block 108 in the above-described unsupervised adaptive adjustment process.

The system 100 can include a configuration input interface fir receiving configuration data, such as but not limited updates to the change factor $\gamma$ and to the training protocol parameter $\tau_p$.

Regarding selection of as to kind and type for the NFB progress feedback rewards, on Applicant's belief, guidelines in selecting which factors to consider, and in the respective weights these can be given in determining the kind(s), type(s), and configuration(s) of training progress rewards, are not necessarily particular to practices according to disclosed embodiments, and therefore are not described in further detail.

Regarding selection of EEG target frequency bands, which determine the configuration of the programmable frequency bandpass filter 106, the selection can be application-specific as it can depend, for example in part, on the particular goals of the NFB training, e.g., improvement of mental concentration, lessening depression, and so forth. Further details of such selection are not necessary to include in this description as persons of skill, upon reading this disclosure, can practice in accordance with its disclosed embodiments using, for purposes of specifying target EEG frequency bands, various selection techniques known to such persons, including but not limited to published databases of correspondence between EEG frequency bands and NFB training goals Example 2

As described above, benefits and advantages provided by systems and methods according to various embodiments include, without limitation, significant reduction in practitioner intervention during NFB sessions. Costs of such intervention include disturbance of the training flow and as indicated, for example, in post NFB training feedback from subjects, disturbance and annoyance of the subjects.

Table 1 below presents a data of a subject in the study, using unsupervised adaptive threshold as calculated in real-time in accordance with disclosed embodiments. The training used for the Table 1 data was up-training $\tau_p=1$, and used $\gamma=0.1$ as increase in threshold value. The training used an initial mean neuromarker $\mu_0$ based on eyes-open EEG data.

Then $T_{k+g}$ unsupervised adaptive threshold adjustment was performed, for k=1, 2, 3, . . . , K. The window size, G, was 20 samples, and the sampling frequency was 500 samples/sec. The subject applied effort to achieve the power of target frequency band and once the threshold was achieved in the target frequency band, the reward was given in terms of points as a part of NFB training. This provided a near real-time NFB training with an unsupervised adaptive threshold which motivated the subject to train the subject's brain activity to achieve an increase in the target frequency band power.

TABLE 1

Trajectory of Unsupervised Adaptive Threshold Adjustment Generated for Up-Training of Alpha Frequency Band Power, Using Adaptive Increase in the Previous Value of $\gamma = 0.1$.

| | 0.1 | |
|---|---|---|
| $\gamma$ | 1 | |
| $\tau_p$ k | $\mu_{k+g}$ ($\alpha$ training) | $T_{k+g}$ |
| 0 | 3.56 | 3.916 |
| 1 | 3.35 | 3.685 |
| 2 | 4.11 | 4.521 |
| 3 | 3.87 | 4.257 |
| 4 | 3.61 | 3.971 |
| 5 | 3.49 | 3.839 |
| 6 | 4.13 | 4.543 |
| 7 | 4.32 | 4.752 |
| 8 | 4.59 | 5.049 |
| 9 | 4.47 | 4.917 |
| 10 | 4.91 | 5.401 |
| . | . | . |
| . | . | . |
| . | . | . |

Example 3

Figure 2:
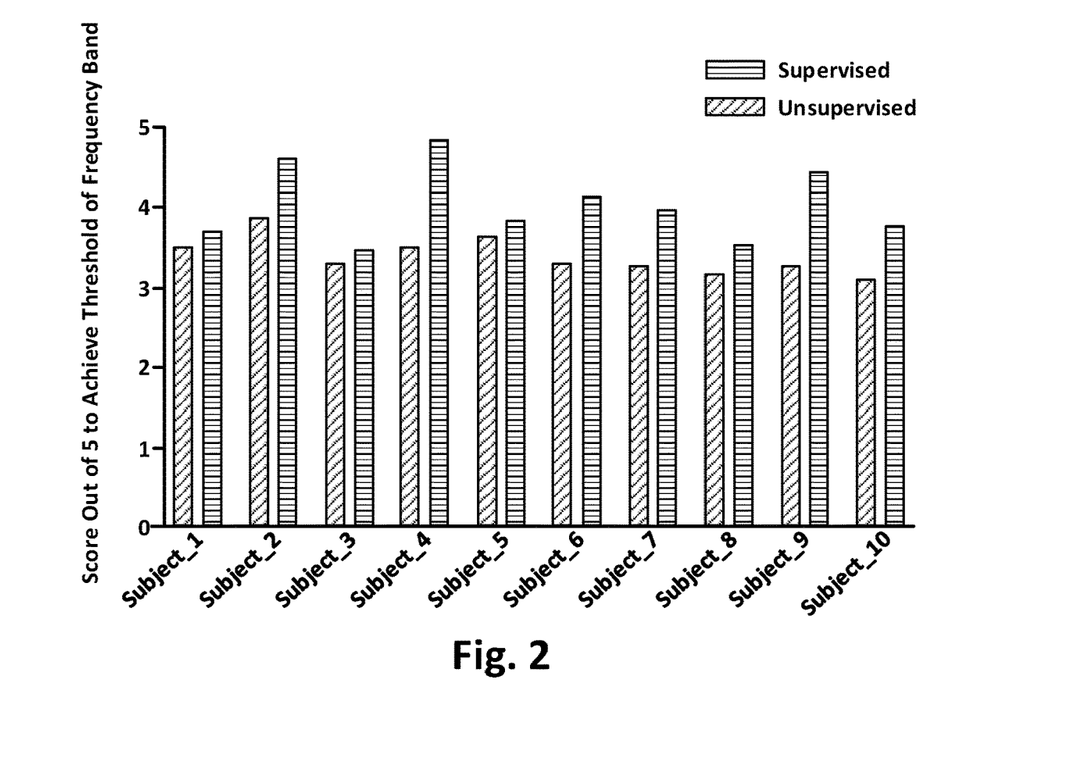
FIG. 2 shows a comparison of improvements in alpha asymmetry measured as attained by a set of subjects at completion of a general practice NFB training program against improvements, for the same subjects, in alpha asymmetry measured as attained at completion of an NFB training program featuring unsupervised adaptive threshold selection in accordance with one or more disclosed embodiments.

Applicant performed a study NFB training of 10 subjects, with a test objective of improvement in alpha asymmetry. The study NFB training included use of unsupervised adaptive threshold adjustment in accordance with one or more embodiments, and use of supervised, practitioner intervention based, threshold adjustment. Study results are shown in FIG. 2. The data, as visible in FIG. 2, shows that the 10 subjects received more rewards, meaning their efforts more likely to be successful in moving toward the target frequency band power than efforts using with supervised threshold selection.

Example 4

Figure 3:
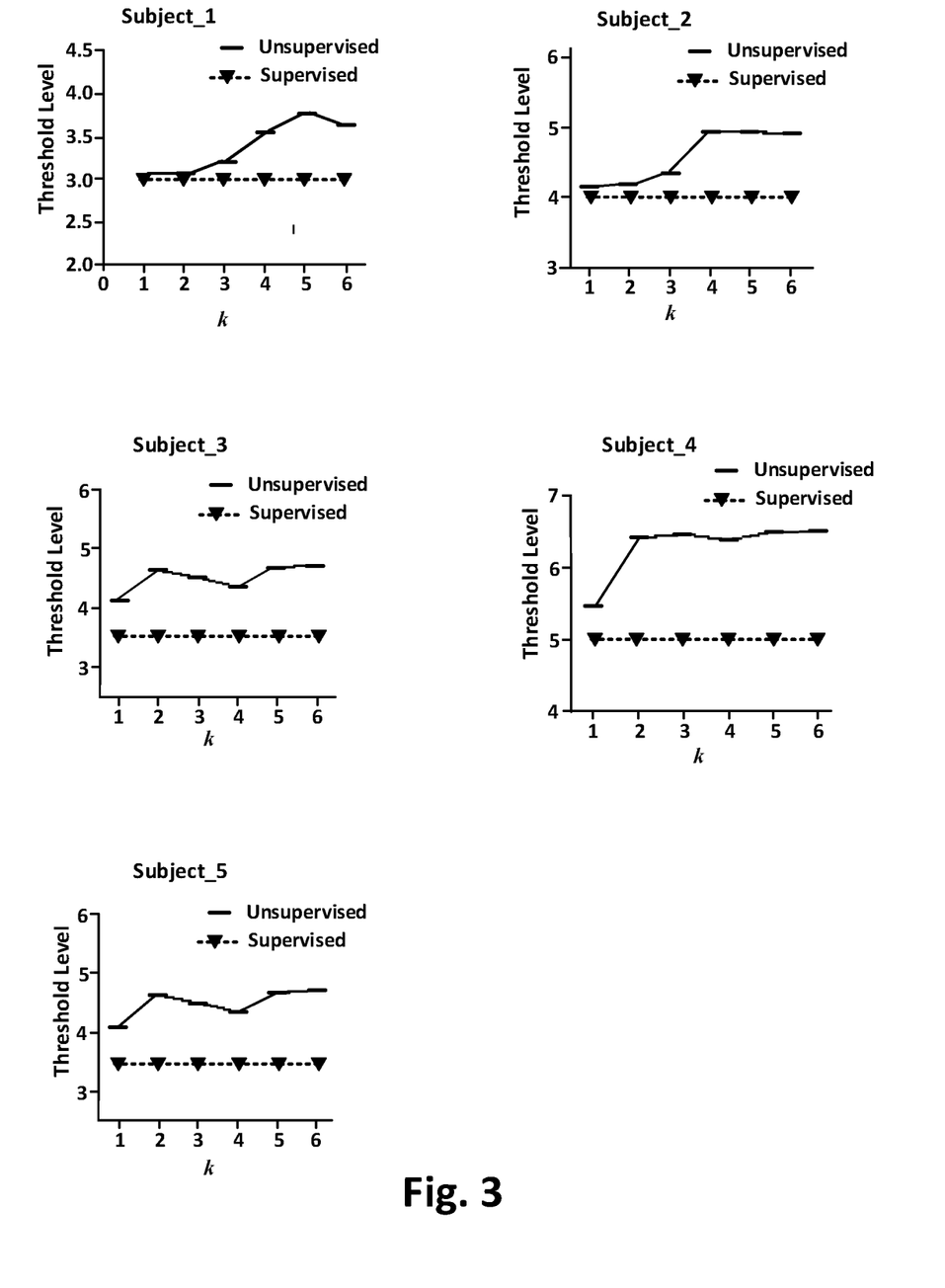
FIG. 3 shows a threshold adaptively changed according to the up-training of target frequency band power to provide a better reward system during NFB
Figure 4:
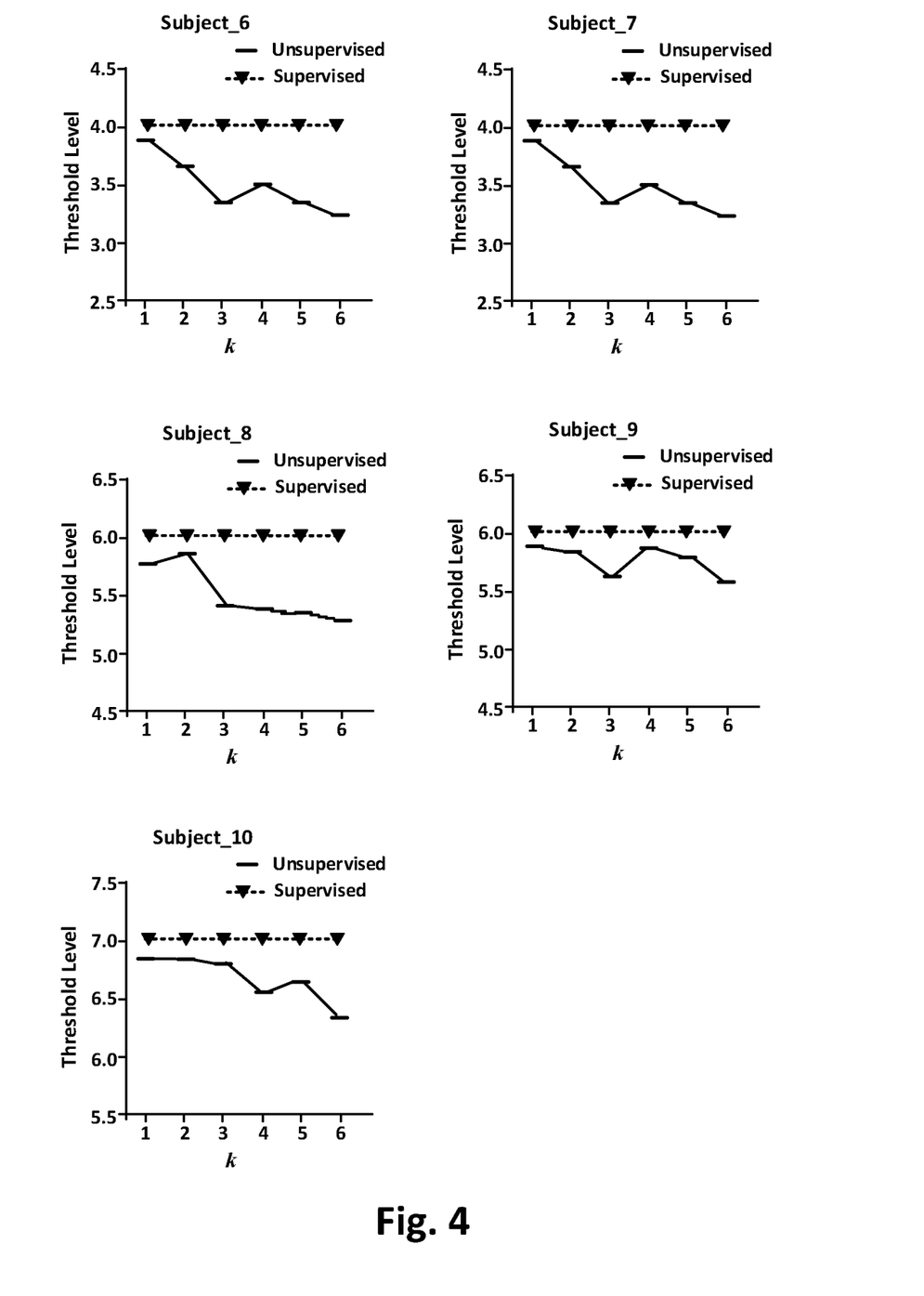
FIG. 4 shows an unsupervised adaptive threshold in NFB training changed according to the neuromarker to provide a better reward in down-training, while the supervised threshold remained fixed during the NFB training.

FIG. 3 shows individual results for each subject for up-training unsupervised adaptive threshold adjustment in accordance with one or more embodiments, and using of supervised, practitioner intervention based, threshold adjustment. FIG. 4 shows individual results for each subject for down-training unsupervised adaptive threshold adjustment in accordance with one or more embodiments, and using of supervised, practitioner intervention based, threshold adjustment.

As clear from FIG. 3 and FIG. 4, the individual results for each subject using the showed better results of achieving target frequency band power using unsupervised adaptive threshold adjustment in accordance with one or more embodiments, than exhibited using the supervised threshold which, as can be seen, remains fixed once selected for a session of NFB.

Example 5

Figure 5:
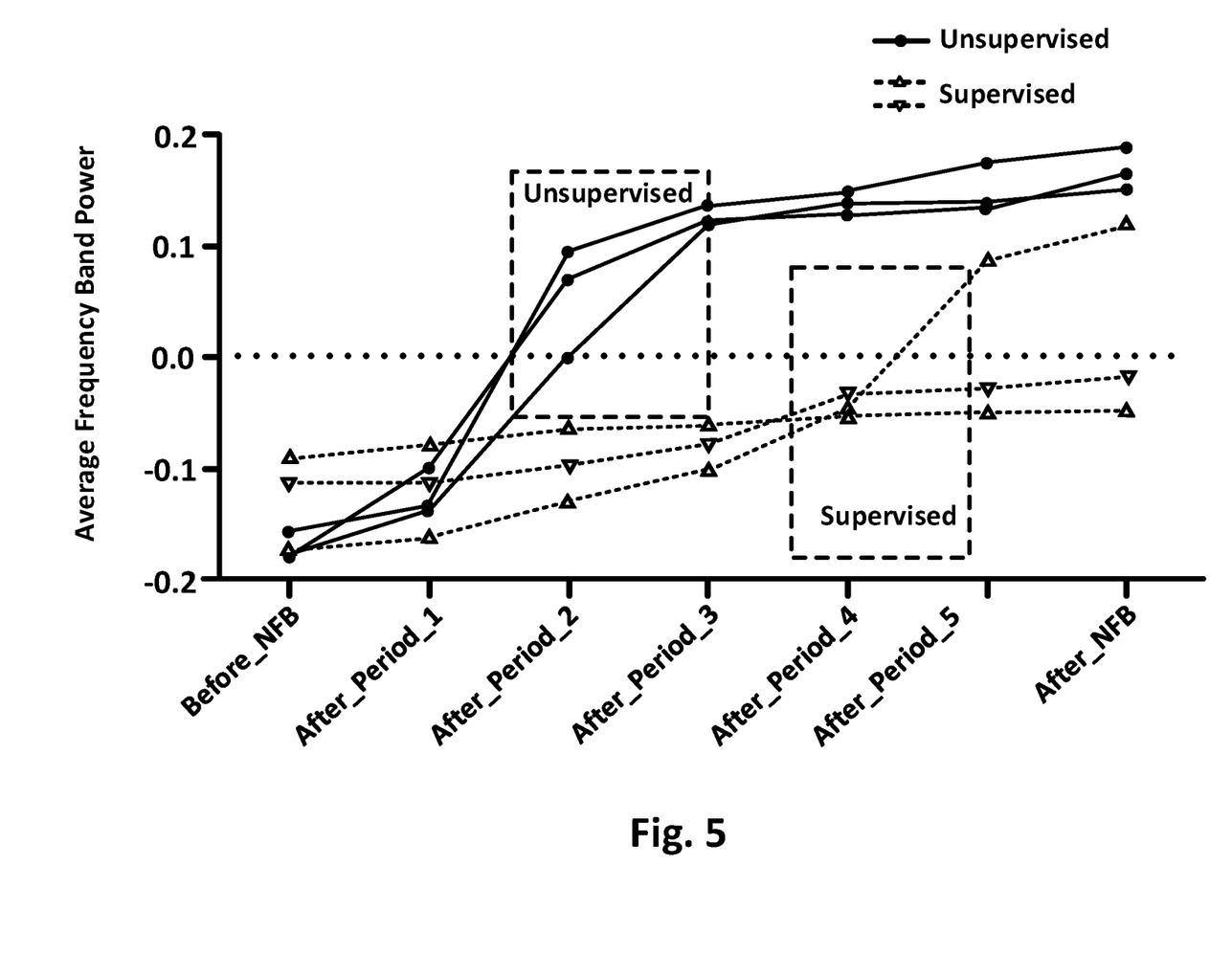
FIG. 5 shows a target frequency band power achieved the threshold levels in the NFB training with automatic unsupervised adaptive threshold earlier (2nd/3rd Period) as compared to the supervised threshold (5th Period) for NFB training.

FIG. 5 shows analysis results, that show that unsupervised adaptive threshold adjustment in accordance with various embodiments obtained, for test subjects, earlier achievement in the target frequency band power at the second to the third period in a session than achieved using the supervised threshold where the brain activity achieved the target frequency band power after the fourth and fifth period in a session. This shows improvement is NFB efficacy through unsupervised adaptive threshold adjustment, namely reducing the time to achieve the brain activity to target frequency band power.

Example 6

Figure 6:
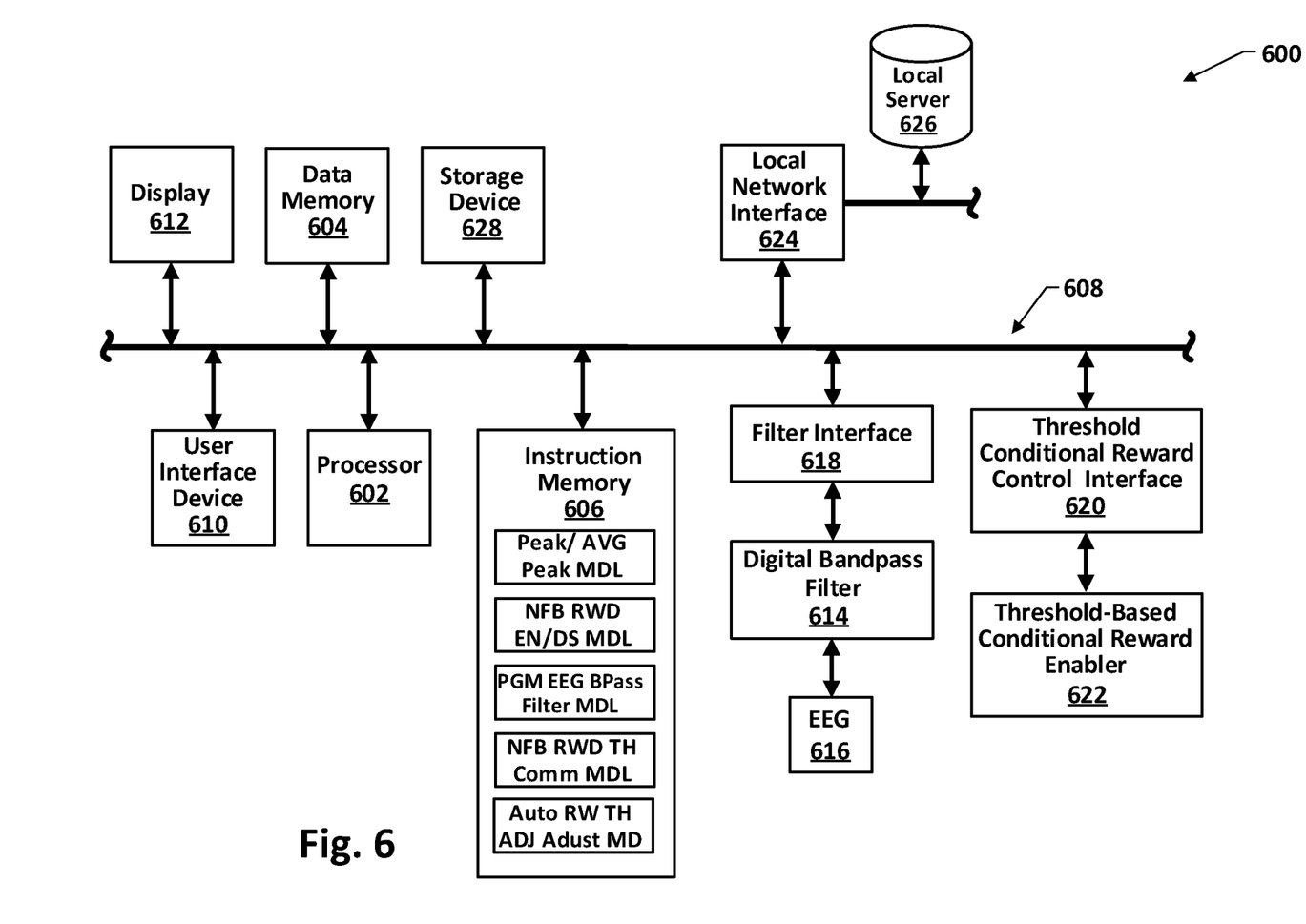
FIG. 6 shows a logic schematic of an example programmable computer system on which systems and methods in accordance with various embodiments may be practiced.

FIG. 6 shows a logic schematic of an example programmable computer-based system 600, hereinafter "system 600," for AUA threshold adjustment in accordance with various embodiments. Referring to FIG. 1, the computing system 600 can implement, for example, the AUA threshold adjustment system 110 and can support methods for AUA threshold adjustment, e.g., as described in reference to FIG. 1 and elsewhere in this disclosure.

As shown in FIG. 6, the system 600 can include a processor 602, which can be connected to a data memory 604 and an instruction memory 606 by, for example, a bus 608. Referring to FIG. 6, it will be understood that the graphic blocks visible on the figure referenced, e.g., blocks referenced here as processor 602, data memory 604, and instruction memory 606, as well as bus 608, are functional blocks, which are not necessarily descriptive of, and are not limitations on hardware architecture, or allocations of functions to hardware, or distribution of functionalities between software and hardware. For example, and without limitation, the data memory 604 and instruction memory 606 may be virtual memory resources, e.g., storage space in a memory device or a distribution of memory devices, or can be an-board memory resource of, for example, an integrated circuit (IC) implementation of the processor 602.

The computer system 600 can further comprise a user interface device 610, e.g., a keyboard, and can include a display 612, which that may also, implement the user interface device 612, e.g., as a touchscreen. FIG. 6 shows a digital bandpass filter 614, which can connect to an external EEG device 616, and can provide the above-described FIG. 1 frequency bandpass filtering 108. In an implementation, the digital bandpass filter 614 can be an external device that can interface to the bus 608, e.g., by a filter interface 618.

FIG. 6 shows a block 620 labeled "threshold-based reward enabler," which represents a computerized threshold conditional presenting, or enablement of presenting a reward stimulus to the subject. The threshold-based reward enabler 620 can be a processing resource of a computer external to the system 600, and in such implementations block 620 can interface to the bus 608, e.g., by a threshold-based reward interface 622. The threshold-based reward enabler 620 can alternatively be the processor 602 and appropriate instructions sin the instruction memory 606.

The computer system 600 may connect the processor 602, e.g., via the bus 608 or otherwise and a local network interface 624, to a local server 626. The computer system 600 may also include a mass storage device 628, e.g., a disc drive or solid state storage device. Executable instructions stored in the instruction memory 606 can be organized or grouped, in a virtual sense, into "modules." The organization does not necessarily mean organization with respect to locations in memory, or separation according to module. For example blocks of instruction code may be shared among multiple modules. In the FIG. 6 configuration, the modules can include a peak detection, average peak, mean of average peak module, such the example represented by the block labeled "PEAK/AVG Peak MD," and an automatic reward threshold adjust control module, represented by the block labeled "Auto RW TH ADJ Adjust MD." Modules stored in the instruction memory 606 can also include an NFB reward threshold communication module, such as the sample represented by the block labeled "NFB RWD TH Comm MDL."

In an embodiment, the Auto RW TH ADJ Adjust MD module may control triggering of the processor 602 performing the unsupervised adaptive adjusting of the reward threshold, e.g., by triggering execution of PEAK/AVG Peak MDL to perform the adjusting, e.g., as described above in reference to Fig. block 102. In one or more embodiments, the Auto RW TH ADJ Adjust MD control may be based, as also described above, on a number of shift-in-shift-out increments of the EEG sample stream through a buffer implementation of the running time window. The NFB RWD TH Comm MDL may include instructions for the processor 602 to communicate the adjusted reward threshold value to a controller of providing and not providing the reward stimulation to the subject in the training sessions. The FIG. 6 schematic includes representation of such a module, namely the block labeled "NFB RWD TH Comm MDL."

According to various embodiments, control of conditional enabling—disabling of a providing of a feedback reward to a subject active in an ongoing EEG training session may be external to the system 600. In other embodiments, system 600 can control the conditional presenting of the feedback reward to the subject. In such embodiments, the described enable-disable function can be provided by an available capacity of the processor 602 in combination with feedback reward enable-disable control instructions stored in the instruction memory 606. FIG. 6 shows an example of such instruction, represented by the block labeled "NFB RWD EN/DS MDL." An illustrative example of a conditional deliverer of an NFB training feedback to the subject, the condition being EEG signals showing progress in the subject's efforts to change said signals to the target state. An illustrative example of the reward can be a high quality rendition of an emotionally uplifting or otherwise noticeably pleasing audiovisual content. An example disabling of the reward, e.g., in response to detecting the subject's brainwaves not being sufficiently close to, or not having moved sufficiently closer to the target state, can be a terminating or disabling, or lowering the quality of the audiovisual content.

As described above in reference to system 100, in one or more embodiments a system, such the system 100, for automatic, unsupervised, adaptive adjusting of the reward threshold may provide the programmable digital bandpass filters XXX. Referring to FIG. 6, an example implementation of system 600 includes a particularly configured resource providing the programmable digital bandpass filters, namely, a portion of the processing capacity of the processor 602 in combination with instructions, such represented by the block labeled "PGM EEG Bandpass Filter MDL."

The instruction memory 606 can comprise a computer-readable media, for example and without limitation, FLASH memory, Secure Digital Random Access Memory (SDRAM), Random Access Memory (RAM), Read Only Memory (ROM), Programmable Read-Only Memory (PROM), Erasable Programmable Read-Only Memory (EPROM), Electrically Erasable Programmable Read Only Memory (EEPROM), solid-state hard disk or any other information processing device with which the processing circuit communicates, such as a server or computer.

Further, the advancements may be provided as a utility application, background daemon, or component of an operating system, or combination thereof, executing in conjunction with MPU 300 and a mobile operating system such as Android, Microsoft™ Windows™ 10 Mobile, Apple iOS™ and other systems known to those skilled in the art.

The requisite hardware elements may be implemented by various circuitry elements known to those skilled in the art. For example, MPU 300 may be a Qualcomm mobile processor, a Nvidia mobile processor, an Atom™ processor from Intel Corporation of America, a Samsung mobile processor, or an Apple A7 mobile processor, or may be other processor types that would be recognized by one of ordinary skill in the art. Alternatively, the MPU 300 may be implemented on an Field-Programmable Gate Array (FPGA), Application Specific Integrated Circuit (ASIC), Programmable Logic Device (PLD) or using discrete logic circuits, as one of ordinary skill in the art would recognize. Further, MPU 300 may be implemented as multiple processors cooperatively working in parallel to perform the instructions of the inventive processes described above.

Other elements of the system may optionally include a network controller, such as an Intel Ethernet PRO network interface card from Intel Corporation of America, for interfacing with a network. As can be appreciated, the network can be a public network, such as the Internet, or a private network such as LAN or WAN network, or any combination thereof and can also include PSTN or ISDN sub-networks. The network can also be wired, such as an Ethernet network. The processing circuit may include various types of communications processors for wireless communications including 3G, 4G and 5G wireless modems, Wi-Fi, Bluetooth™, GPS, or any other wireless form of communication that is known.

A display controller, such as a NVIDIA™ GeForce™ GTX or Quadro™ graphics adaptor from NVIDIA Corporation of America, may be included for interfacing with a display of the classification results. An I/O interface may interface with e.g. volume control, a microphone, one or more cameras, an audio input or output circuit, etc. The classification results may be output to a screen that is a touch screen, various support elements of which may include Industry Standard Architecture (ISA), Extended Industry Standard Architecture (EISA), Video Electronics Standards Association (VESA), Peripheral Component Interface (PCI), or similar, for interconnecting all of the system.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The authors extend their appreciation to the Deputyship for Research & Innovation, Ministry of Education in Saudi Arabia for funding this research work through the project number 2021-154 with IFPRC-018-135-2020 and King Abdulaziz University, DSR, Jeddah, Saudi Arabia.

We claim:

1. A method for unsupervised adaptive threshold neurofeedback (NFB) training, comprising:
   a processor receiving and storing a time window of samples of target frequency bands from an electroencephalogram (EEG) measuring of brain wave signals of a subject in an NFB training session and based at least in part on the stored time window of samples performing an unsupervised adaptive adjustment of an NFB reward threshold comprising processor steps of:
   determining neuromarker values in the time window of samples, based at least in part on peak values of the target frequency bands over the time window,
   computing the mean value of the neuromarker values over the time window,
   computing an adaptive adjusted NFB reward threshold, based at least in part on a multiplication product of a reward threshold adjustment factor, a training protocol value, and the computed mean value of the neuromarker values, and
   communicating the computed adaptive adjusted NFB reward threshold to an NFB controller; and
   the NFB controller using the computed adaptive adjusted NFB reward threshold as a feedback reward threshold for contingent delivery or non delivery of a feedback reward to the subject.

2. The method of claim 1 for unsupervised adaptive threshold NFB training, further comprising the processor step of performing the unsupervised adaptive adjustment of the NFB reward threshold being a real-time step, the real-time step extending a time span, the time span being less than the time duration of the time window.

3. The method of claim 2 for unsupervised adaptive threshold NFB training, wherein:
   the samples of target frequency bands correspond to a sample-per-second sampling of EEG measurement signals, and
   the time window is a running time window comprising a shift-in-shift-out memory resource that holds integer G of the target frequency band samples.

4. The method of claim 1 for unsupervised adaptive threshold NFB training, wherein the unsupervised adaptive adjustment of the NFB reward threshold value is further based, at least in part, on the arithmetic sum of the mean value of the neuromarker values and the multiplication product of the mean value of the neuromarker values, the reward threshold adjustment factor, and the training protocol value.

5. The method of claim 1 for unsupervised adaptive threshold NFB training, wherein determining the neuromarker values in the time window comprises:
   detecting periodic signals within the time window of samples of the target frequency bands, and
   determining peak amplitudes of the detected periodic signals over the time window.

6. The method of claim 1 for unsupervised adaptive threshold NFB training, further comprising:
   receiving, at a digital frequency bandpass filter configured to pass the target frequency bands, a sample stream of digitized EEG signals from the EEG measuring; and
   the digital frequency bandpass filter outputting the samples of target frequency bands.

7. The method of claim 1 for unsupervised adaptive threshold NFB training, further comprising initializing the feedback reward threshold for the NFB controller to an initial reward threshold value, the initializing comprising:
   the processor receiving and storing an initialization time window of samples of frequency bands from a preliminary EEG measuring of brainwave signals of the subject over an eyes-open resting state session, and computing, based at least in part on the initialization time window of samples, the initial reward threshold value, by steps comprising:
   determining preliminary neuromarker values in the initialization time window of samples, based at least in part on peak values of the frequency bands over the initialization time window,
   computing the mean value of the preliminary neuromarker values over the initialization time window,
   computing the initial reward threshold value based at least in part on a multiplication product of the reward threshold adjustment factor, the training protocol value, and the computed mean value of the preliminary neuromarker values, and communicating the computed initial feedback reward threshold value to the NFB controller; and the NFB controller using the computed initial feedback reward threshold value as an initial feedback reward threshold for the contingent delivery or non delivery of the feedback reward to the subject.

\* \* \* \* \*